United States Patent
Cahill et al.

(10) Patent No.: US 7,623,690 B2
(45) Date of Patent: *Nov. 24, 2009

(54) SYSTEM AND METHOD FOR CLASSIFYING IN VIVO IMAGES ACCORDING TO ANATOMICAL STRUCTURE

(75) Inventors: Nathan D. Cahill, West Henrietta, NY (US); Marvin M. Goodgame, Ontario, NY (US); Shoupu Chen, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 1345 days.

This patent is subject to a terminal disclaimer.

(21) Appl. No.: 10/812,785

(22) Filed: Mar. 30, 2004

(65) Prior Publication Data

US 2005/0228293 A1   Oct. 13, 2005

(51) Int. Cl.
*G06K 9/00* (2006.01)
*A61B 5/05* (2006.01)

(52) U.S. Cl. .................. 382/128; 382/224; 600/424

(58) Field of Classification Search .......... 382/100, 382/128, 129, 130, 131, 132, 133, 134, 154, 382/156, 162, 170, 181, 190–199, 224, 232, 382/260, 274, 276, 291, 305; 345/440; 600/407, 600/424; 707/10
See application file for complete search history.

(56) References Cited

U.S. PATENT DOCUMENTS

| | | | |
|---|---|---|---|
| 5,604,531 A | 2/1997 | Iddan et al. | 348/76 |
| 6,826,422 B1 * | 11/2004 | Modell et al. | 600/407 |
| 6,950,690 B1 * | 9/2005 | Meron et al. | 600/424 |
| 7,215,338 B2 * | 5/2007 | Horn et al. | 345/440 |
| 7,490,085 B2 * | 2/2009 | Walker et al. | 707/10 |

FOREIGN PATENT DOCUMENTS

| | | |
|---|---|---|
| EP | 1 159 917 A1 | 12/2001 |
| WO | WO 00/22975 | 4/2000 |
| WO | WO 01/65995 | 9/2001 |
| WO | WO 01/87377 | 11/2001 |
| WO | WO 02/36007 A1 | 5/2002 |
| WO | WO 02/073507 A2 | 9/2002 |
| WO | WO 02/095351 A2 | 11/2002 |
| WO | WO 02/100256 A2 | 12/2002 |
| WO | WO 02/102223 A2 | 12/2002 |

* cited by examiner

*Primary Examiner*—Seyed Azarian

(57) ABSTRACT

A system for identifying anatomical structure depicted in an in vivo image, that includes an examination bundlette having a captured in vivo image; and a gastrointestinal atlas that includes a list of individual anatomical structures and characterization data of the individual anatomical structures. A classification engine analyzes the examination bundlette and the gastrointestinal atlas to identify the anatomical structure depicted in the captured in vivo image.

24 Claims, 4 Drawing Sheets

SYSTEM AND METHOD FOR CLASSIFYING IN VIVO IMAGES ACCORDING TO ANATOMICAL STRUCTURE

FIELD OF THE INVENTION

The present invention relates generally to an in vivo camera system and, in particular, to classifying images captured by an in vivo camera system according to anatomical structure.

BACKGROUND OF THE INVENTION

Several in vivo measurement systems are known in the art. They include swallowable electronic capsules which collect data and which transmit the data to a receiver system. These intestinal capsules, which are moved through the digestive system by the action of peristalsis, are used to measure pH ("Heidelberg" capsules), temperature ("CoreTemp" capsules) and pressure throughout the gastrointestinal (GI) tract. They have also been used to measure gastric residence time, which is the time it takes for food to pass through the stomach and intestines. These intestinal capsules typically include a measuring system and a transmission system, where a transmitter transmits the measured data at radio frequencies to a receiver system.

U.S. Pat. No. 5,604,531, assigned to the State of Israel, Ministry of Defense, Armament Development Authority, and incorporated herein by reference, teaches an in vivo measurement system, in particular an in vivo camera system, which is carried by a swallowable capsule. In addition to the camera system there is an optical system for imaging an area of the GI tract onto the imager and a transmitter for transmitting the video output of the camera system. The overall system, including a capsule that can pass through the entire digestive tract, operates as an autonomous video endoscope. It images even the difficult to reach areas of the small intestine.

FIG. 1 shows a block diagram of the in vivo video camera system described in U.S. Pat. No. 5,604,531. The system captures and transmits images of the GI tract while passing through the gastrointestinal lumen. The system contains a storage unit 100, a data processor 102, a camera 104, an image transmitter 106, an image receiver 108, which usually includes an antenna array, and an image monitor 110. Storage unit 100, data processor 102, image monitor 110, and image receiver 108 are located outside the patient's body. Camera 104, as it transits the GI tract, is in communication with image transmitter 106 located in capsule 112 and image receiver 108 located outside the body. Data processor 102 transfers frame data to and from storage unit 100 while the former analyzes the data. Processor 102 also transmits the analyzed data to image monitor 110 where a physician views it. The data can be viewed in real time or at some later date.

During a typical examination, the in vivo camera system may take anywhere from about four to eight hours or more to traverse the digestive tract. Assuming a capture rate of about 2 images per second, the total number of captured images can range from approximately 35,000 to 70,000 or more. If these images were subsequently displayed as a video sequence at a rate of 30 frames per second, one would require 20-40 minutes of viewing time to observe the entire video. This estimate does not include the extra time needed to zoom in and/or decrease the frame rate for a more detailed examination of suspect areas.

In some situations, the physician may desire to view only a portion of the video related to a certain anatomical structure. For example, if Crohn's disease is suspected based on symptoms such as abdominal pain, weight loss, iron deficiency anemia, diarrhea, an elevated erythrocyte sedimentation rate, or fever, then the in vivo camera system might be used to locate ulcerations within the small intestine. In this case, the physician may be interested in viewing only the segment of the video pertaining to the small intestine, and may not have the time or inclination to cue the video manually to find the beginning of the small intestine.

One remedy to this situation is to limit the capture frequency of the in vivo camera system until the capsule reaches the small intestine. For example, PCT Application WO 01/65995, assigned to Given Imaging Ltd., discloses a system for shutting down the imager and other device electronics for a period of approximately two hours until the capsule reaches the small intestine. This period of approximately two hours is derived solely from the known average motility of the human digestive tract. It does not rely on any patient specific information. Patient specific motility information can be used to adjust the capture frequency of the in vivo camera system, as is described in PCT Application WO 01/87377, also assigned to Given Imaging Ltd. However, neither average motility information nor patient specific motility information is enough to accurately pinpoint the anatomical structure or structures being captured in particular in vivo images or video segments.

PROBLEM TO BE SOLVED BY THE INVENTION

The present invention solves the problem of presenting the physician with pertinent in vivo images or video segments of a specific anatomical structure, without requiring the physician to cue an entire in vivo video manually in order to find the desired anatomical structure. Furthermore, the present invention solves the problem of adjusting the capture frequency of the in vivo camera system in accordance with the anatomical structure or structures being captured.

SUMMARY OF THE INVENTION

The aforementioned need is met according to the present invention by providing a system for identifying anatomical structure depicted in an in vivo image. The present invention includes an examination bundlette having a captured in vivo image; and a gastrointestinal atlas that includes a list of individual anatomical structures and characterization data of the individual anatomical structures. A classification engine analyzes the examination bundlette and the gastrointestinal atlas to identify the anatomical structure depicted in the captured in vivo image.

ADVANTAGEOUS EFFECT OF THE INVENTION

The present invention has the following advantages: First, automatic classification of in vivo images according to anatomical structure enables the physician to view in vivo images of a specific anatomical structure or structures without having to waste valuable time in manually searching the in vivo video. Second, adjusting the capture rate enables any desired anatomical structure to be imaged more frequently than non-desired anatomical structures. This provides a mechanism for yielding a more detailed analysis of the desired anatomical structure to the physician, while simultaneously optimizing the power consumption of the in vivo capsule.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

To facilitate understanding, identical reference numerals have been used, where possible, to designate identical elements that are common to the figures.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

During a typical examination of a body lumen, the in vivo camera system captures a large number of images. The images can be analyzed individually, or sequentially, as frames of a video sequence. An isolated image or frame without context has limited value. Some contextual information is frequently available prior to or during the image collection process; other contextual information can be gathered or generated as the images are processed after data collection. Any contextual information will be referred to as metadata. Metadata is any information that is not pixel data, such as the image header data that accompanies many digital image files.

Figure 1:
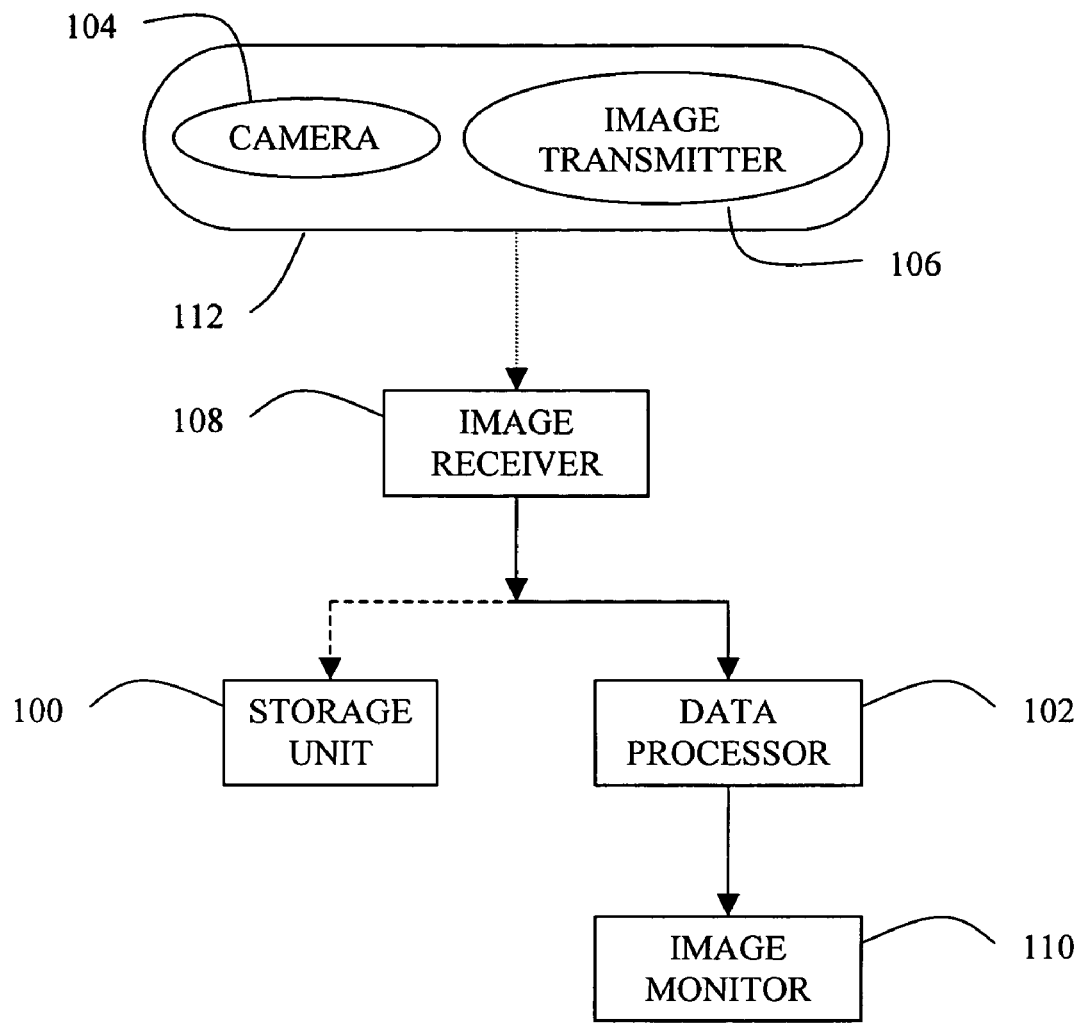
FIG. 1 (PRIOR ART) is a block diagram illustration of an in vivo camera system.
Figure 2A:
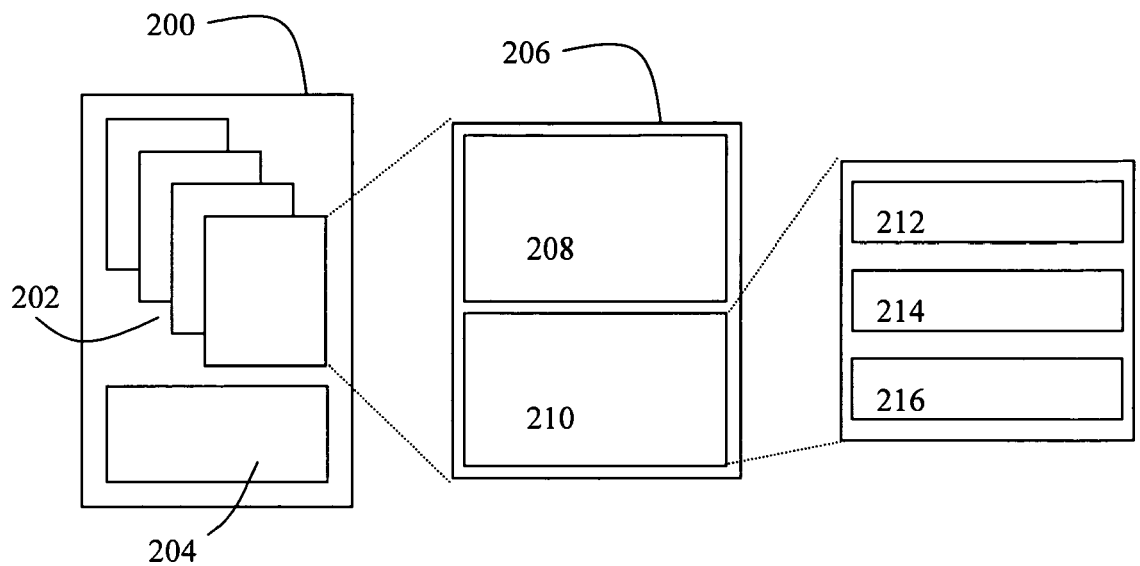
FIG. 2A is an illustration of an examination bundle.

Referring to FIG. 2A, the complete set of all images captured during the examination, along with any corresponding metadata, will be referred to as an examination bundle 200. The examination bundle 200 consists of a collection of image packets 202 and a section containing general metadata 204.

An image packet 206 comprises two sections: the pixel data 208 of an image that has been captured by the in vivo camera system, and image specific metadata 210. The image specific metadata 210 can be further refined into image specific collection data 212, image specific physical data 214 and image specific inferred data 216. Image specific collection data 212 contains information such as the frame index number, frame capture rate, frame capture time, and frame exposure level. Image specific physical data 214 contains information such as the relative position of the capsule when the image was captured, the distance traveled from the position of initial image capture, the instantaneous velocity of the capsule, capsule orientation, and non-image sensed characteristics such as pH, pressure, temperature, and impedance. Image specific inferred data 216 includes location and description of detected abnormalities within the image, and any pathologies that have been identified. This data can be obtained either from a physician or by automated methods.

The general metadata 204 contains such information as the date of the examination, the patient identification, the name or identification of the referring physician, the purpose of the examination, suspected abnormalities and/or diagnosis, and any information pertinent to the examination bundle 200. It can also include general image information such as image storage format (e.g., TIFF or JPEG), number of lines, and number of pixels per line. It will be understood and appreciated that the order and specific contents of the general metadata or image specific metadata may vary without changing the functionality of the examination bundle.

Figure 2B:
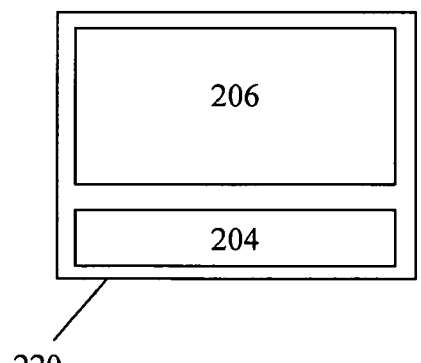
FIG. 2B is an illustration of an examination bundlette.

In some scenarios, general metadata 204 may be required before the examination bundle 200 has been fully constructed. For example, a physician may wish to monitor captured images in real time as the capsule passes through the GI tract in order to closely search a region for a suspected abnormality. In these scenarios, we will encapsulate the general metadata 204 with a specific image packet 206 to form an examination bundlette 220, as illustrated in FIG. 2B.

Figure 3:
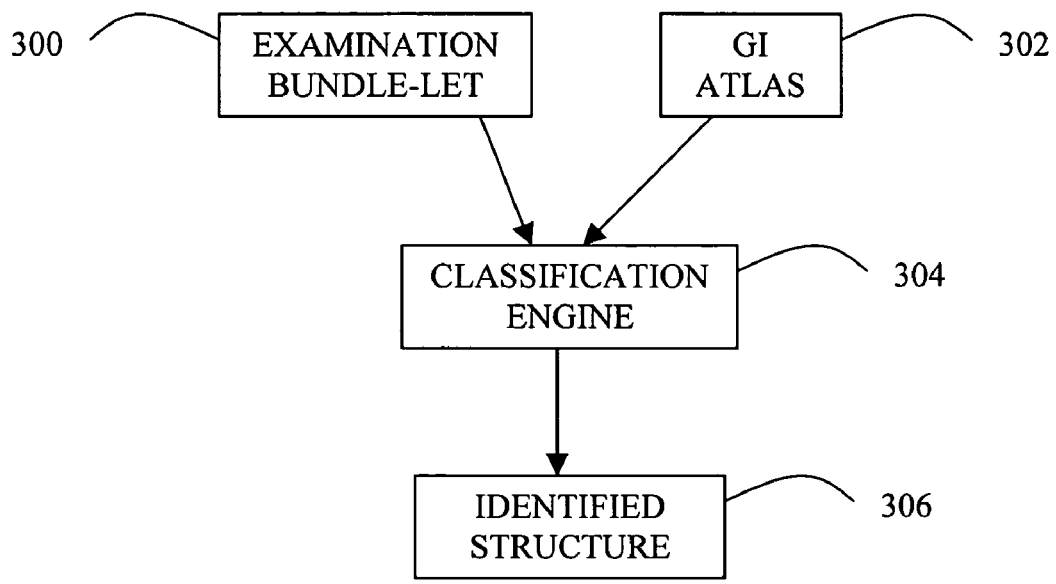
FIG. 3 is a block diagram illustration of the system of the current invention for identifying anatomical structure depicted in an in vivo image.

The present invention describes a method and system for identifying the anatomical structures pertaining to specific images or video segments captured by the in vivo camera system. FIG. 3 illustrates a system for identifying the anatomical structure pertaining to a specific image. The system takes as input an examination bundlette 300 and a GI atlas 302, and passes them into a classification engine 304. The classification engine 304 identifies the anatomical structure pertaining to the image packet of the examination bundlette 300, and yields as output the identified anatomical structure 306.

Figure 4:
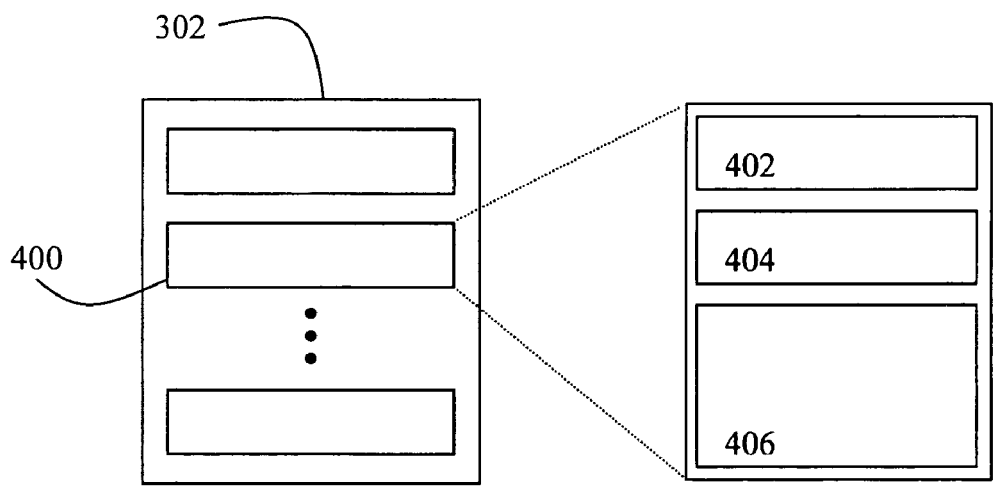
FIG. 4 is an illustration of a GI atlas.

FIG. 4 illustrates the GI atlas 302 that is provided to the classification engine 304 of FIG. 3. The GI atlas 302 is defined to be a list of anatomical structures, along with any pertinent characterization data for each individual anatomical structure. In the preferred embodiment, the list of anatomical structures includes the mouth, pharynx, esophagus, cardiac orifice, stomach, pylorus, duodenum, jejunum, ileum, ileocecal valve, cecum, colon, rectum, and anus. This list is not restrictive, however; other embodiments may include a subset of these anatomical structures, a more detailed set of anatomical structures, or a combination of structures (e.g., small intestine instead of duodenum, jejunum, and ileum). For a specific anatomical structure 400, pertinent characterization data may include a structure label 402, non-image specific characterization data 404, and image specific characterization data 406. The structure label can simply be the anatomical name of the structure, such as mouth, pharynx, etc., or an index or key denoting the structure. Characterization data can include any type of data that describes or characterizes the anatomical structure. Non-image specific characterization data 404 can include the average length or size of the structure, average relative position of the structure along the GI tract and/or with respect to other anatomical structures, average pH, temperature, and pressure levels of the structure, average motility characteristics of the structure, etc. Image specific characterization data 406 can include representative images of the anatomical structure captured from various positions and orientations, and from various illumination levels, color and/or texture distributions or features of representative images of the structure, etc. Characterization data is not limited to the specific types of data described herein; rather, any data deemed pertinent to the identification of anatomical structure can be included in the non-image specific or image specific characterization data.

The classification engine 304 takes as input an examination bundlette 300 and the GI atlas 302, and executes a method for identifying the particular structure in the GI atlas 302 that is imaged in the examination bundlette 300. A variety of classification methods, among them image and non-image based classification methods, can be executed by the classification engine 304. For an in-depth discussion of classification methods, see R. O. Duda and P. E. Hart, *Pattern Recognition and Scene Analysis*, New York: John Wiley, 1973. In the preferred embodiment, a supervised learning scheme is used to perform the classification. One or more feature vectors are derived from the non-image specific characterization data 404 and/or image specific characterization data 406 for each structure, generating prototypes describing each anatomical structure. These prototypes can be generated prior to classification of a particular examination bundlette; in the preferred embodiment, they are generated prior to the examination and stored in the characterization data of the GI atlas 302.

A feature vector is then derived from the general metadata 204, the pixel data 208, and/or the image specific metadata 210 of the examination bundlette 300. The derived feature vector is then classified to the class described by the prototypes of a particular anatomic structure. This classification can be performed in many different ways. If the class whose centroid is closest to the derived feature vector is chosen, the classifier is the well-known minimum mean Euclidean distance classifier. If the class containing the maximum number of neighbors out of the k nearest neighbors to the derived feature vector is chosen, the classifier is the well-known k-nearest neighbor classifier. Other types of classifiers can be used as well, such as linear, piecewise linear, quadratic, or polynomial discriminant functions, decision trees, neural networks, support vector machines, or the like. In this way, the classification of the derived feature vector by the classification engine 304 identifies the anatomical structure 306 associated with the examination image bundlette 300.

A number of embodiments of the present invention are possible depending on the choice of characterization data used to generate the prototypes and the feature vector of the examination bundlette. For example, in one embodiment, the prototypes are constructed solely with features from the image specific characterization data 406 for each structure in the GI atlas 302. Such features could include color information, texture information, morphological information, or any information extracted from representative images of each anatomical structure. Whatever features are used to construct the prototypes should also be the features extracted from the examination bundlette prior to classification. In another embodiment, the prototypes are constructed solely with features from the non-image specific characterization data 404 for each structure in the GI atlas 302. For example, prototypes can be constructed with features that describe the length, absolute position, and/or relative position of the anatomical structures within the GI tract. The classification engine 304 can extract the position information of the capsule from the examination bundlette 300, integrate the position information to determine the absolute distance traveled, and identify the anatomical structure by choosing the one whose absolute position is the same as the absolute distance traveled. In another embodiment, the prototypes are constructed with both the non-image specific characterization data 404 and the image specific characterization data 406. For example, prototypes can be constructed with features derived both from the image data itself, and from the position data of the capsule.

Figure 5:
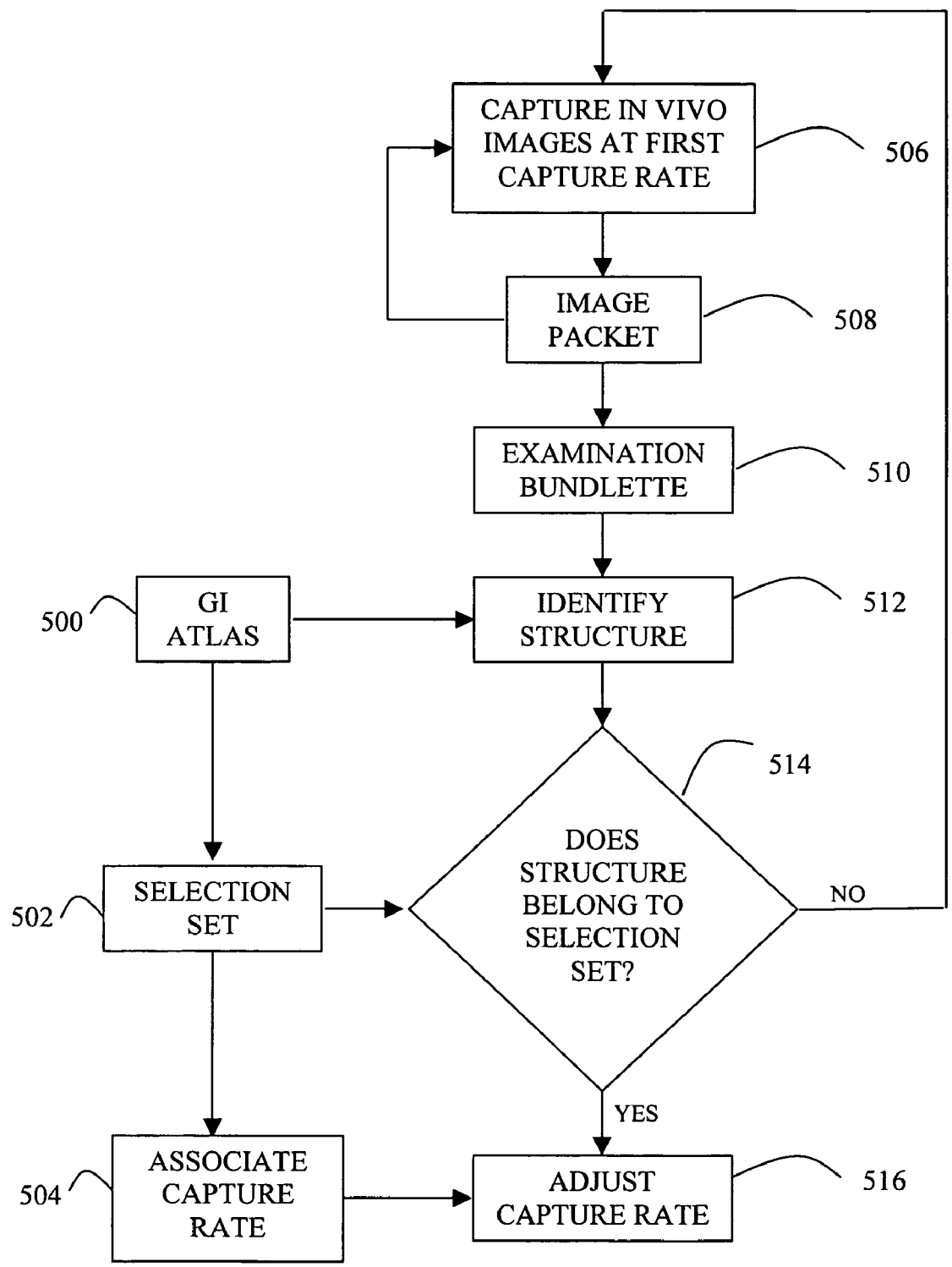
FIG. 5 is a block diagram illustration of the method of the current invention for adjusting the capture frequency of an in vivo camera system.

FIG. 5 is a block diagram illustration of a method for adjusting the capture rate of an in vivo camera system in accordance with anatomical structure. A GI atlas 500, as described in FIG. 4, is provided. Next, a selection set 502 is constructed containing at least one anatomical structure 400 from the GI atlas 500. Next, a capture rate is associated 504 with each anatomical structure in the selection set 502. If the selection set 502 contains more than one anatomical structure, then the capture rates for two or more of the anatomical structures in the selection set may be identical, or the capture rates for each anatomical structure in the selection set may be unique. In the preferred embodiment, the selection set contains one or more anatomical structures of interest to the physician. For example, if Crohn's disease is suspected, the physician may only be interested in images of the small intestine. In this example, the selection set 502 may be chosen to contain only the duodenum, jejunum, ileum, and the capture rates 504 associated with these structures are chosen to be larger than the default capture rate of the in vivo system.

Now, in step 506, in vivo images are captured at a first capture rate. Every time an in vivo image is captured, an image packet 508 is produced, as described in the description of FIG. 2A. For at least one image packet 508, an examination bundlette 510 is formed, as described in the description of FIG. 2B. The examination bundlette 510 and GI atlas 500 are input into the system of FIG. 3, which, in step 512, identifies the anatomical structure imaged in the examination bundlette. Upon identification of the anatomical structure 512, a query 514 is made as to whether the identified anatomical structure 512 is an element of the selection set 502. An affirmative response to query 512 indicates that the first capture rate of the in vivo camera system is adjusted 516 to the capture rate 504 associated with the identified anatomical structure 512. A negative response to query 512 indicates that the first capture rate remains unchanged.

The method illustrated in FIG. 5 can be extended to account for different capture rates associated with more than one anatomical structure. For instance, after the capture rate adjustment step 516, the first capture rate can be redefined as the adjusted capture rate, and steps 506 through 516 can be repeated. This entire process can be continued for the duration of an in vivo examination. In addition, this process can encapsulate situations where the physician wants the in vivo camera system to return to a default capture rate when the identified anatomical structure is not contained in the selection set. This is accomplished by taking all of the anatomical structures that are listed in the GI atlas 500 but not in the selection set 502, including them in the selection set 502, and associating with them the default capture rate in step 504.

The invention has been described in detail with particular reference to certain preferred embodiments thereof, but it will be understood that variations and modifications can be effected within the spirit and scope of the invention.

PARTS LIST

100 Storage Unit
102 Data Processor
104 Camera
106 Image Transmitter
108 Image Receiver
110 Image Monitor
112 Capsule
200 Examination Bundle
202 Image Packets
204 General Metadata
206 Image Packet
208 Pixel Data
210 Image Specific Metadata
212 Image Specific Collection Data
214 Image Specific Physical Data
216 Image Specific Inferred Data
220 Examination Bundlette
300 Examination Bundlette
302 GI Atlas 304 Classification Engine
306 Identified Structure
400 Anatomical Structure
402 Structure Label
404 Non-Image Specific Characterization Data
406 Image Specific Characterization Data
500 GI Atlas
502 Selection Set
504 Associate Capture Rate Step
506 Capture In Vivo Images Step
508 Image Packet
510 Examination Bundlette
512 Identify Structure Step
514 Query
516 Adjust Capture Rate Step

What is claimed is:

1. A system for identifying anatomical structure depicted in an in vivo image, comprising:
   a) an examination bundlette that includes an in vivo image;
   b) a gastrointestinal atlas that includes a list of individual anatomical structures and characterization data of the individual anatomical structures; and
   c) a classification engine that analyzes the examination bundlette and the gastrointestinal atlas to identify the anatomical structure depicted in the in vivo image.

2. The system claimed in claim 1, wherein the classification engine includes a classifier identifying the anatomical structure depicted in the in vivo image.

3. The system claimed in claim 2, wherein the classifier is selected from the group consisting of k-nearest neighbor, linear, piecewise linear, quadratic, or polynomial discriminant functions, decision trees, neural networks, and support vector machines.

4. The system claimed in claim 1, wherein the classification engine uses image based classification methods for analyzing the examination bundlette and the gastrointestinal atlas.

5. The system claimed in claim 1, wherein the classification engine extracts image based features from the examination bundlette for comparison with image specific characterization data in the gastrointestinal atlas.

6. The system claimed in claim 1, wherein the classification engine extracts non-image based features from the examination bundlette for comparison with non-image specific characterization data in the gastrointestinal atlas.

7. The system claimed in claim 5, wherein the image specific characterization data is selected from the group consisting of representative images of the anatomical structure captured from various positions and orientations, from various illumination levels, color and/or texture distributions, and features of representative images of the anatomical structure.

8. The system claimed in claim 6, wherein the non-image specific characterization data is selected from the group consisting of the average length or size of the anatomical structure, average relative position of the anatomical structure along the gastrointestinal tract and/or with respect to other anatomical structures, average pH, temperature, pressure levels of the anatomical structure, and average motility characteristics of the anatomical structure.

9. The system claimed in claim 1, wherein the gastrointestinal atlas includes a list of anatomical structures selected from the group consisting of the mouth, pharynx, esophagus, cardiac orifice, stomach, pylorus, duodenum, jejunum, ileum, ileocecal valve, cecum, colon, rectum, and anus.

10. A method for identifying anatomical structure depicted in an in vivo image, the method being carried by an in vivo camera system and comprising the steps of
    a) providing an examination bundlette that includes an in vivo image;
    b) providing a gastrointestinal atlas that includes a list of individual anatomical structures and characterization data of the individual anatomical structures; and
    c) analyzing the examination bundlette and the gastrointestinal atlas to identify the anatomical structure depicted in the in vivo image.

11. The method claimed in claim 10, wherein the classification engine includes a classifier for identifying the anatomical structure depicted in the captured in vivo image.

12. The method claimed in claim 11, wherein the classifier is selected from the group consisting of k-nearest neighbor, linear, piecewise linear, quadratic, or polynomial discriminant functions, decision trees, neural networks, and support vector machines.

13. The method claimed in claim 10, wherein the classification engine uses image based classification methods for analyzing the examination bundlette and the gastrointestinal atlas.

14. The method claimed in claim 10, wherein the classification engine extracts image based features from the examination bundlette for comparison with image specific characterization data in the gastrointestinal atlas.

15. The method claimed in claim 10, wherein the classification engine extracts non-image based features from the examination bundlette for comparison with non-image specific characterization data in the gastrointestinal atlas.

16. The method claimed in claim 14, wherein the image specific characterization data is selected from the group consisting of representative images of the anatomical structure captured from various positions and orientations, from various illumination levels, color and/or texture distributions, and features of representative images of the anatomical structure.

17. The method claimed in claim 15, wherein the non-image specific characterization data is selected from the group consisting of the average length or size of the anatomical structure, average relative position of the anatomical structure along the gastrointestinal tract and/or with respect to other anatomical structures, average pH, temperature, pressure levels of the anatomical structure, and average motility characteristics of the anatomical structure.

18. The method claimed in claim 10, wherein the gastrointestinal atlas includes a list of anatomical structures selected from the group consisting of the mouth, pharynx, esophagus, cardiac orifice, stomach, pylorus, duodenum, jejunum, ileum, ileocecal valve, cecum, colon, rectum, and anus.

19. A system for identifying anatomical structure depicted in an in vivo image, comprising:
    a) an examination bundlette that includes a captured in vivo image;
    b) a gastrointestinal atlas that includes a list of individual anatomical structures and characterization data of the individual anatomical structures; and
    c) a means for analyzing the examination bundlette and the gastrointestinal atlas to identify the anatomical structure depicted in the captured in vivo image.

20. The system claimed in claim 19, wherein the means for analyzing the examination bundlette and the gastrointestinal atlas includes a classifier for identifying the anatomical structure depicted in the captured in vivo image.

21. The system claimed in claim 20, wherein the classifier is selected from the group consisting of k-nearest neighbor, linear, piecewise linear, quadratic, or polynomial discriminant functions, decision trees, neural networks, and support vector machines.

22. The system claimed in claim 19, wherein the means for analyzing the examination bundlette and the gastrointestinal atlas uses image based classification methods for analyzing the examination bundlette and the gastrointestinal atlas.

23. The system claimed in claim 19, wherein the means for analyzing the examination bundlette and the gastrointestinal atlas extracts image based features from the examination bundlette for comparison with image specific characterization data in the gastrointestinal atlas.

24. The system claimed in claim 19, wherein the means for analyzing the examination bundlette and the gastrointestinal atlas extracts non-image based features from the examination bundlette for comparison with non-image specific characterization data in the gastrointestinal atlas.

* * * * *